United States Patent [19]
Geho et al.

[11] Patent Number: 4,767,615
[45] Date of Patent: * Aug. 30, 1988

[54] DENTAL THERAPY BY VESICLE DELIVERY
[75] Inventors: W. Blair Geho; Joseph Jacob; John R. Lau, all of Wooster, Ohio
[73] Assignee: Technology Unlimited, Inc., Wooster, Ohio
[*] Notice: The portion of the term of this patent subsequent to Jul. 29, 2003 has been disclaimed.
[21] Appl. No.: 877,862
[22] Filed: Jun. 24, 1986

Related U.S. Application Data
[63] Continuation-in-part of Ser. No. 606,714, May 3, 1984, Pat. No. 4,603,044.
[51] Int. Cl.$^4$ .............................................. A61K 7/16
[52] U.S. Cl. ........................................ 424/57; 424/49; 424/54
[58] Field of Search ............... 424/19, 21, 22, 27, 424/28, 38, 49, 54, 57

[56] References Cited
U.S. PATENT DOCUMENTS
4,483,929 11/1984 Szaka ................................. 435/7
4,603,044 7/1986 Geho ................................. 514/3

OTHER PUBLICATIONS
*Accepted Dental Therapeutics*, 38th Ed., American Dental Association, Chicago, Ill. 1979, p. 343.
Jones et al. in *Chemical Week*, McGraw-Hill Inc., Jul. 30, 1986, pp. 426–5129, "Liposome Research: New Path for Drug Delivery".

*Primary Examiner*—Ronald W. Griffin
*Assistant Examiner*—F. T. Moezie
*Attorney, Agent, or Firm*—Frijouf, Rust & Pyle

[57] ABSTRACT

A known procedure is used to prepare liposomes of bipolar lipid membrane which are permeable and hence "leak" their contents at a rate which is variable by choice. The liposome is supplied with medication or cosmetic material for the oral cavity, or specifically for the teeth and gums. The liposome is then attached to a molecule that has affinity for the hydroxyapatite. Thus, the liposome will bind to oral cavity hydroxyapatite and bathe the surrounding support surface with its contents for extended hours of service.

2 Claims, 5 Drawing Sheets

| Sample | Core volume constituents | Membrane constituents | Weight in mg. | Target molecule | Weight in mg. | Setting | Sonication Time in minutes | Temp. °C ± 0.5°C | Annealing time in min |
|---|---|---|---|---|---|---|---|---|---|
| 1 | 10 mM Phosphate buffer, pH 7.4 | $^{14}C$-DSL<br>DSL<br>LysoDSL<br>CHOL | (21.72)<br>(7.24)<br>(1.64) | PG | (2.0) | 4 | 10 | 60 | 10 |
| 2 | 10 mM Phosphate buffer, pH 7.4 | $^{14}C$-DSL<br>DSL<br>LysoDSL<br>CHOL | (28.96)<br>(9.65)<br>(1.67) | 4,5-Diphosphate | (1.82) | 4 | 5 | 60 | 5 |
| 3 | $^{14}C$ β-D-glucose in $H_2O$ 1 mg/ml | DSL<br>CHOL | (38.61)<br>(1.67) | 4,5-Diphosphate | (0.2) | 4 | 7 | 60 | 7 |
| 4 | $^{14}C$ β-D-glucose in $H_2O$ 1 mg/ml | DSL<br>CHOL | (38.61)<br>(1.67) | 4,5-Diphosphate | (0.2) | 4 | 7 | 60 | 7 |
| 5 | $^{14}C$ β-D-glucose in $H_2O$ 1 mg/ml | DSL<br>CHOL<br>4,5-Diphosphate<br>Cr | (38.61)<br>(1.67)<br>(0.2)<br>(0.087) | Dequest | (1.51) | 4 | 7 | 60 | 7 |

Abbreviations: DSL - L-α Distearoyl Lecithin (2 acyl chains)
LysoDSL - L-α Monostearoyl Lecithin (1 acyl chain)
CHOL - Cholesterol
4,5-Diphosphate - Phosphatidyl Inositol-4,5-Diphosphate
PG - Phosphatidyl glycerol

DENTAL THERAPY BY VESICLE DELIVERY

CROSS REFERENCE TO RELATED APPLICATION

This invention is a continuation-in-part of application Ser. No. 606,714, filed May 3, 1984, now issued as U.S. Pat. No. 4,603,044.

BACKGROUND OF THE INVENTION

1. Field of the Invention

A chemically-structured delivery system for targeting liposomes containing medication to the tooth structure of the oral cavity.

2. Description of Prior Art

A general background for understanding the chemical process steps that go into making vesicles and liposomes is set forth clearly in a publication "Biochemistry" by Lubert Stryer, published by W. H. Freeman and Company, San Francisco, Calif., U.S.A., copyright 1981.

The repertoire of membrane lipids is extensive, and Stryer states they may even be bewildering, but they do possess a critical common structural theme in that membrane lipids contain both a hydrophilic and hydrophobic moiety.

A space-filling model of a typical lipid has a general shape roughly rectangular with two fatty acid chains approximately parallel to one another and a hydrophilic moiety pointing in the opposite direction.

It is common practice to use a short hand illustration which has been adopted to represent these membrane lipids. The hydrophilic unit called the polar head group is represented by a circle and the hydrocarbon tails are represented by lines which may be straight or wavy.

The polar head groups have affinity for water and the hydrocarbon tails avoid water and seek lipid media. A bi-molecular sheet, known also as a lipid bi-layer, is the favored structure for most phospholipids and glycolipids in aqueous media.

The structure of a bi-molecular sheet is inherent in the structure of lipid molecules. Their formation is a rapid and spontaneous process in water. Hydrophobic interaction is the major driving force for the formation of lipid bi-layers. It is important to the final construction of a targeted liposome that there are van der Waals attactive forces between the hydrocarbon tails. These van der Waals forces favor close packing of the hydrocarbon tails, and also will accept the hydrocarbon moiety of target molecules from an aqueous solution.

Clustering of bipolar lipids is favored by the van der Waals attractive forces with the significant biological consequence that they will tend to close on themselves so that there are no ends with exposed hydrocarbon chains and therefore result in the formation of a compartment which is normally self sealing because a hole in a bi-layer is energetically unfavorable.

However, if one of the lipid components of such a closed compartment has one R-group missing, there will be a fault dislocation which defeats the self sealing behavior and allows the contents of the liposome to leak from the inner aqueous compartment.

Therefore, as explained in the prior art and particularly in the Stryer publication supra, liposomes are aqueous compartments enclosed by a lipid bi-layer. They can be formed by suspending a suitable lipid, such as phosphatidyl choline in an aqueous medium. This mixture is then sonicated, which is an agitation by high frequency sound waves, to give a dispersion of closed liposomes that are quite uniform in size. There are other methods of forming such liposomes, and one specific recommended procedure is set forth in the specification hereinafter.

Molecules, such as sodium fluoride for dental therapy, can be trapped in the aqueous compartment of liposomes by forming them in the presence of these substances. For example, if liposomes as small as 500 Å in diameter are formed in a 0.1M glycine solution, Stryer states that about 2000 molecules of glycine will be trapped in each inner aqueous compartment. This manner of packaging oral cavity enhancement chemicals is the first step of the present invention.

The biochemistry of the polyphosphoinositides and the diphosphonates as noted in the scientific literature demonstrates that these molecules are capable of participating in chemical reactions that result in the formation of exceptionally strong coordination complexes with the calcium ions of the hydroxyapatite crystal over a very broad pH range.

SUMMARY OF THE INVENTION

Lipid vesicles, otherwise known as liposomes, are envelopes having, in part, a lipophilic membrane. Basically, the vesicle walls are composed of bipolar molecules having a lipophilic end and a hydrophilic end. These molecules are intertwined with the hydrophilic ends forming inner and outer walls with the lipophilic ends sandwiched therebetween.

This invention employes vesicles whose membrane is permeable and contain entrapped chemicals useful for oral cavity enhancement, such as fluorides, antiplaque materials and breath fresheners. Permeability is usually accomplished by the use of lysolecithin as a wall membrane component. A full teaching of liposomal membranes containing lysolecithin is contained in the 1976 addition of the Journal of Biochemistry wherein the work of Takayuki Kitagawi, Keizo Inoue and Shoshichi Nojima, department of chemistry, National Institute of Health, Kamiosaki, Shinagawa-Ku, Tokyo, Japan, describing liposomes which have been prepared with lysolecithin, lecithin, dicetyl phosphate and cholesterol. This report states that generally, lysolecithin incorporation decreases the effectiveness of the membranes as a barrier to glucose and made the membranes more "osmotically fragile". This terminology simply means that by including lysolecithin a fault dislocation is produced in the membrane wall, allowing the contents to leak from the vesicle. The amount of the lysolecithin incorporation will decidedly influence the rate at which the vesicles will leak the contents. Relatively low concentrations of lysolecithin cause an increase in the permeability of the liposomes, this report states. These studies suggested that the induction of a change in the molecular organization by lysolecithin molecules may cause the permeability change.

Since the work published by the National Institute of Health in Tokyo, the manufacture of vesicles from totally non-leaking structure to those which quickly lose their contacts, is now fully developed and well known prior art.

This invention provides a means whereby the permeable liposome, with its cargo of oral cavity enhancement material, anchored to tooth structure of the oral cavity in order that eating, drinking and normal saliva wash will not dislodge the vesicle. Keeping it in place until the contents are fully expanded is the touchstone of this invention.

A long chain target molecule is composed having one end lipophilic and the other end characterized by the ability to chemisorb with the surface of hydroxyapatite crystals. The lipophilic end is caused to penetrate the hydrophilic wall of the liposome and form weak van der Waals bonds characterized as a transient attraction, with the lipophilic membrane. The hydrophilic end of the target molecule will then project from the liposome.

The resultant composition when exposed to tooth or bone hydroxyapatite will cause an attempt by the hydrophilic end of the target molecule to form strong bident metal ligands with the hydroxyapatite in a chemical bond.

The normal chemical relationship of the chelating hydrophilic end would be to form a chelate ring with calcium, but because the calcium of tooth structure is a component of the hydroxyapatite, the attraction which anchors the hydrophilic end of the target molecule is better characterized as chemisorption.

The net result of this invention is that a permeable liposome, having a core volume of an oral cavity enhancement chemical, is attached to the tooth structure by exposing the tooth to a wash or other carrier containing the targeted structure of this invention.

DEFINITIONS

Vesicle—Substantially spherical thin walled bladder, usually in a range of about 250 Å to 1500 Å.

Liposome—A larger spherical bladder, often of layered walls, ranging from about 1000 Å to several micron.

For the purpose of this teaching, a target molecule may be a chemical structure directly connected to a liposome and having a hydrophilic moiety capable of chemisorptive bonding to hydroxyapatite, or it may be a composite (conjugate) molecule with two separate molecules joined by a bridge, thereby establishing a lipophilic moiety and a hydrophilic moiety.

DESCRIPTION OF THE DRAWINGS

FIG. 2 is a list of the sample codes, lipid constituents, weights in mg., sonication and annealing times and temperatures and conditions under which the various vesicle preparations are made.

DESCRIPTION OF THE PREFERRED EMBODIMENT

Figure 1:
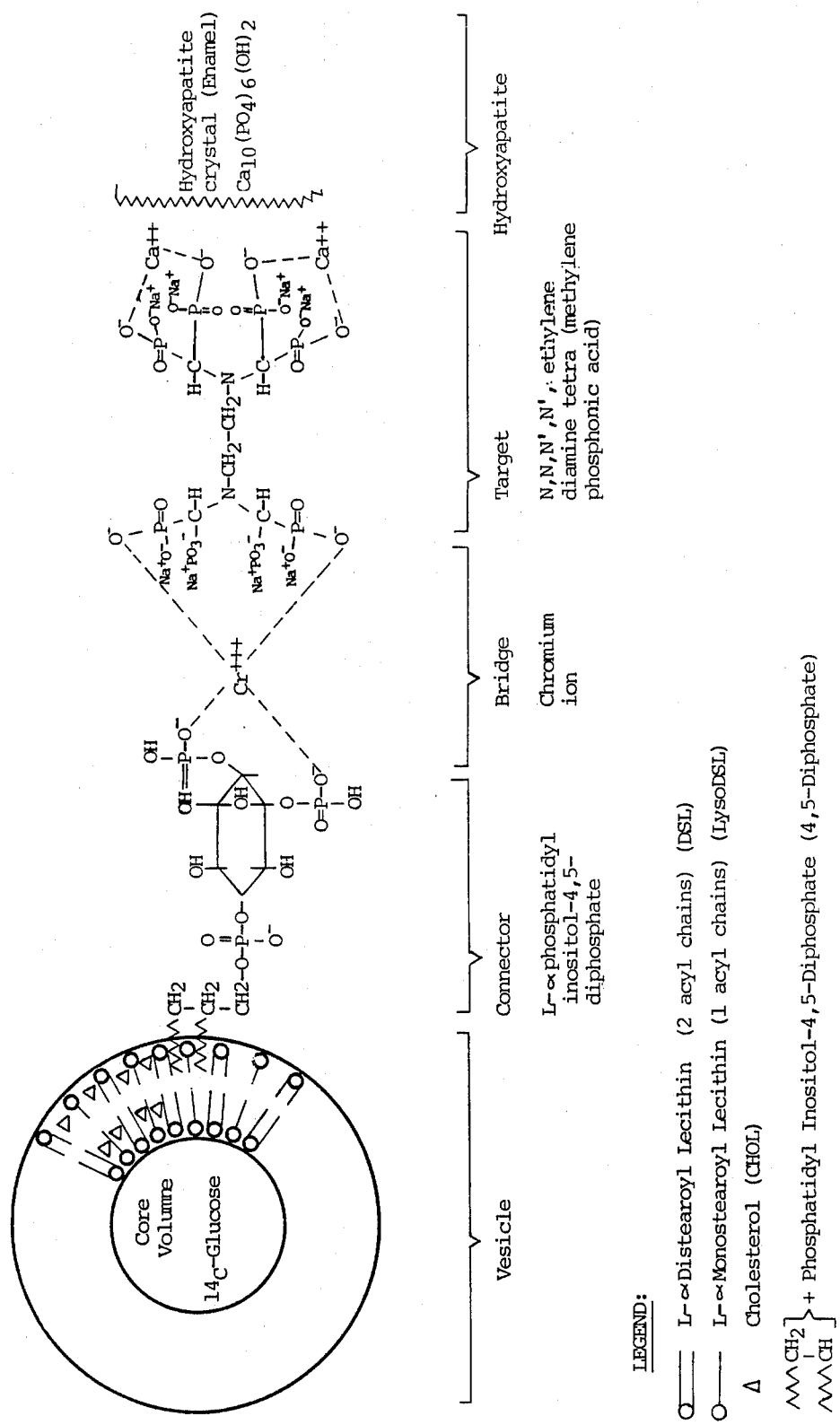
FIG. 1 is a structural representation of a unilamellar liposome carrying a core volume of radioactive trace material for delivery to tooth hydroxyapatite, and a target anchoring molecule linking the liposome to the surface of a tooth.

The primary object of this invention is to provide a sustained release mechanism for medical and cosmetic materials in the oral cavity of a warm-blooded animal.

It is well known that treatment of dental carries and peridontal problems is carried out in the dental office by application of liquid fluoride solutions and gels, or by incorporation such medication into toothpaste and mouthwashes.

The effectiveness of such procedures is the product of concentration and time in contact with the treated areas. The dentist uses a very high concentration of the fluoride medication in the liquid or gel and washes the area free of excess material. The dentist thereafter obtains a high degree of effectiveness without danger of adverse effect of ingesting the strong solution. The use of dentifrice is a low concentration application repeated often and is therefore safe for home application.

This invention addresses the growing needs of extended application time of the medical and cosmetic materials in contact with hydroxyapatite and provides a means of effectively treating peridontal disorders as well as those attendant to dental plaque and dental carries, with the goal of providing better dental health care. The invention also addresses the problem of social acceptance by eliminating breath and mouth odors.

The first step in the discovery of this invention was to recognize the capability of incorporating the medical or cosmetic material into a liposome, which liposome is permeable to allow the material contained in the core volume to leak slowly from the vesicle and provide a continuous supply for an extended period of time.

The manufacture and use of liposomes is now well known by organic chemists and researchers. Basically, a liposome is created by sonication of polar lipid material. The liposome will trap a core volume of a water base environment, or will carry lipid materials in the liposome membrane.

Generally, the components of the liposomes are materials such as L-distearoyl lecithin and cholesterol. Sonication causes the lipids to form into spheroidal configuration.

The literature contains much teaching of the actual and proposed uses of liposomes. One structure germane to this present invention is a "leaky" membrane made by introducing reagents which cause fault dislocation. The work of Kitagawa; Inoue, and Nojima, "Properties of Liposomal Membranes Containing Lysolecithin", J. Biochem., 79: 1123–1133 (1976), is an example. In this prior work, liposomes were prepared with lysolecithin, egg lecithin, dicetyl phosphate, and cholesterol. The ability to function as a barrier to the diffusion of glucose marker and the sensitivities of the liposomes to hypotonic treatment and other reagents which modifies the permeability were examined. Generally, lysolecithin incorporation decreased the effectiveness of the membranes as a barrier to glucose and made the membranes more "osmotically fragile", i.e. permeable. Cholesterol incorporation counteracted the effect of incorporated lysolecithin. The more cholesterol incorporated into liposomes, the more lysolecithin could be incorporated into the membrane without loss of function as a barrier.

Therefor, it is known how to capture water soluble substances within a leaky faulted liposome. This invention is directed to attaching a leaky, or sustained release liposomes to the hydroxyapatite. See Kitagawa, Inoue and Nojima, supra.

Using this type of vesicle it has been observed objectively that the treatment materials adhered to the hydroxyapatite for a period of time longer that could be expected of, for example, a mouthwash deodorant.

The present invention was conceived wherein the properties inherent in the unique molecular structure of phosphate compounds that belong to the classes of the polyphosphoinositols and diphosphonates could be employed to bind the vesicle to the hydroxyapatite for increased time of exposure.

Accordingly, a targeted vesicle delivery system has been developed wherein selected phosphate compounds and their derivatives are attached at one end to the lipid vesicle membrane and the other end is available to form strong bidentate metal ligands which result in the formation of coordination complexes with the calcium of the hydroxyapatite lattice of bones and teeth. This attraction is known as chemisorption binding.

One of the important considerations related to the preparation of the delivery system takes into account the fact that the hydroxyapatite of tooth enamel is exposed in the oral cavity to the external environment and thus facilitates the use of a topical vesicle drug delivery system.

According to this invention, the polyphosphoinositides, the diphosphonates and their derivatives have a moiety held to the lipid membrane of a liposome for targeting and subsequent binding of the liposomes to the hydroxyapatite of tooth enamel.

The vesicle delivery system utilizing, for example, the membrane constituent L-$\alpha$phosphatidyl inositol 4,5-diphosphate as a chelating agent for chemisorption binding to hydroxyapatite, suggests a variety of new therapeutic uses for this dental delivery system.

Since the polyphosphoinositides are naturally occurring phospholipids with hydrophilic phospoinositol head groups and hydrophobic fatty acid tail groups, they are uniquely suited for the incorporation into vesicle membranes.

FIG. 1 of the drawings illustrates what is considered to be the preferred embodiment of this invention.

A general definition of the invention is the discovery that an osmotically fragile, i.e. permeable, liposome may be attached to a tooth surface by provision of a molecule having a moiety which is lipophilic and therefore held by van der Waals forces in the lipophilic membrane of the liposome, and a moiety which is hydrophilic and has an affinity for the hydroxyapatite of a tooth surface. Such a structure will bind to the tooth surface for an extended period of time and thereby permit the contents of the liposome to bathe the tooth surface much more efficiently than any available technique known prior to this invention.

In the FIG. 1, a complex molecule is shown as the preferred means to target the liposome to the tooth surface. The connector is bi-polor with one moiety held by van der Waals attraction in the liposome lipid membrane and the other end terminating in oxygen ions.

Note, then, that the portion of the molecule labeled "target" also terminates in oxygen ions which are shown ( . . . ) attracted or bonded to the calcium ion of the hydroxyapatite by chemisorption. The target also has oxygen ions which are connected by bonding forces to a chromium bridge. The chromium bridge connects the oxygen ions of the connector and the target and therefor completes the structure.

It is important to note that the connector L-$\alpha$phosphatidyl inositol 4,5-diphosphate could be connected by bonding directly to the hydroxyapatite without the necessity of the target and bridge illustrated. As stated herein above, the FIG. 1 is the preferred ideal structure and the reason is that the selected target N,N,N',N', ethylene diamine tetra (methylene phosphoric acid), known as Editempa or Dequest produces a minimum etching of tooth surfaces. Although other molecules, such as the connector shown, can bond directly to the tooth surface, it is capable of producing unwanted levels of tooth etching.

Accordingly, those who are skilled in the chemical arts, having this teaching before them, may select from a class consisting of the diphosphonates, the class consisting of the polyphosphoinositides, and the class consisting carboxylic acids, as the preferred general classes of compounds, those which have a moiety which is lipophilic and a moiety which has affinity for the hydroxyapatite. In this selection, those skilled in the art will be able to select various combinations having the required characteristics, and join them by a chemical bridge if desired as taught by the FIG. 1. Otherwise, direct binding is acceptable although in some instances not as desirable as the combination shown in FIG. 1.

To join the moiety by a chromium bridge, the lipid vesicles were collected and then, with respect to the initial concentration of vesicle connector molecules, were reacted with a five-fold molar excess of $CrCl_3$. The vesicles were then rechromatographed using the same buffer to remove unreacted $CrCl_3$. The collected vesicles were then reacted with a five-fold molar excess of connector molecules. Following this step the vesicles were then rechromatographed using the same buffer system to remove unreacted connector molecules. Following the final chromatography, the vesicles were stored under nitrogen in the refrigerator at 5° C.

Because there is no known practical means of measuring the extent to which the present invention effectively delivers and anchors vesicles to the appetite of the oral cavity in vivo, applicant devised a means for establishing the extent of the effectiveness of the present invention. That is, the experiment will demonstrate the affinity of the delivery system for lipids to the hydroxyapatite.

DENTAL DELIVERY SYSTEM (DDS) PREPARATION

The synthetic procedure for the preparation of the targeted dental and drug delivery system is described as follows:

28.96 mg of L $\alpha$distearoyl lecithin and 1.67 mg of cholesterol, for the formation of a bipolar vesicle, plus 1.40 mg of L-$\alpha$phosphatidylinositol-4,5-diphosphate, the target molecule, are solubilized in $CHCl_3$. MeOH (2:1 v/v) and dried under house vacuum for 15 minutes at 60° C.±0.5° C. to form a lipid crust. Following the drying procedure, 2.0 ml of 40 mM $KH_2PO_4$—$K_2HPO_4$, pH 7.4, was added to the lipid crust. The lipid constituents were then sonicated in the cuphorn at 60° C.±0.5° C. for 15 minutes at setting #4 on the sonicator. The sample was then annealed with slow turning at 60°±0.5° C. for 15 minutes. Following the annealing step, the sample was centrifuged in the Triac Clinical Centrifuge on the bloodsetting mode at ambient temperature for 15 minutes. The supernatant containing the lipid suspension was chromatographed over a 1.5 cm×25 cm Sephadex G-100-120 column that had been equilibrated with 40 mM phosphate buffer, pH 7.4. The pooled vesicle fractions collected after chromatography comprised 4.6 ml and were designated as batch 250-E.

This step by step procedure causes on inherent placing the lipophilic part of the target substituent in the lipophilic membranes of the liposome with the hydrophilic head orientated in three-dimensional space extended away from the membrane surface.

CONTROL MATERIAL

A control preparation, referred to hereinafter as 250C, was prepared as described for the DDS, except that no target material was supplied, i.e., material such as the polyphosphoinositides or diphosphonates.

TEST PROCEDURE

This test procedure was chosen to demonstrate the ability of the DDS to bind to hydroxyapatite. The vesicle contents will leak out the medication, breath freshener, of other content as taught by the prior art, and by fixing these vesicles in place on the tooth surface, will be effective in bathing the tooth surfaces and gum tissues for any desired time period. Usually a 24-hour time period will be selected because a fresh supply will normally be presented through tooth brushing of mouthwash at least once in each 24-hour period.

Although the DDS will have for its purpose to bind to dental enamel in the mouth, the laboratory demonstration of the ability of the DDS to bind hydroxyapatite (HA) utilizes the binding of DDS to a fine aqueous suspension of HA purchased from Sigma Chemical Company, St. Louis, Miss. HA is the mineral component of dental enamel. The HA suspension alone will settle out upon standing and leave a perfectly clear supernatant. The DDS preparations (250E and 250C) are bipolar lipid vesicles that form colloidal suspensions. This experiment utilizes both of these attributes: clear, supernatant for HA alone and cloudy supernatant for DDS alone.

If the HA and DDS are combined the resultant supernatant, after permitting settling, can be used to indicate whether or not the DDS became bound to the HA. The two resultant possibilities are:

1. If the resultant supernatant is cloudy, then the HA did not bind the DDS in a significant way.
2. If the resultant supernatant is clear, then the HA bound all of the DDS.

The experiment was designated to demonstrate the enhanced DDS binding to HA when the L-αphosphatidylinositol-4,5-diphosphate was used as a DDS target molecule (preparation 250E) compared to a vesicle with no target molecule (250C).

The experiment test was carried out as follows:

Four test tubes numbered 1–4 were used with numbers 1 and 2 for DDS 250E. Tube numbers 3 and 4 were used for the control vesicles labelled 250C. The additions were according to the following table:

|  | DDS-250E | | Vesicles-250C | |
| --- | --- | --- | --- | --- |
|  | 1 | 2 | 3 | 4 |
| 1.0 ml buffer | X | X | X | X |
| 2 drops HA | X |  | X |  |
| 2 drops buffer |  | X |  | X |
| 0.5 ml 250E | X | X |  |  |
| 0.5 ml 250C |  |  | X | X |

The tubes were covered and stirred with small magnetic stirring bars for 70 hours at room temperature (25° C.) to achieve binding equilibrium. When stirring ceased, the tubes were then allowed to stand overnight to permit the HA to settle. The supernatants were then described:

| Tube #1 | Tube #2 | Tube #3 | Tube #4 |
| --- | --- | --- | --- |
| Clear | Cloudy; no settling of DDS | Cloudy | Cloudy; partial settling of the control vesicles |

The data of tubes 1–4 are interpreted as showing a complete binding of the DDS-250E to HA as evidence by the clear supernatant in Tube #1. The lack of settling in Tube #2 indicates that the DDS 250E, which did not have hydroxyapatite solution to bind to, is a stable colloid that does not spontaneously settle. Tube #2 is a control for Tube #1.

Tube #3 had a cloudy supernatant, indicating that the control vesicles of batch 250C (the vesicles without target molecules) did not bind efficiently to the HA. Close examination indicated, however, a weak binding of some vesicles. The partial settling of Tube #4 indicates that the vesicles without the target molecule is a less stable colloid than the complete DDS 250E.

The conclusion is that the DDS-250E by virtue of the L-αphosphatidylinositol-4,5-diphosphate target molecule does efficiently bind the HA, which is the mineral component of dental enamel.

The important conclusion to be made from these observations is that a binding profile can be depicted extending from the weak interaction of the control vesicles to the strong interaction with hydroxyapatite as evidenced by the experimental sample. The fact that there is weak vesicle adherence by hydroxyapatite, as well as strong adherence, introduces the option of manufacturing vesicles that either bind weakly or strongly to hydroxyapatite, depending upon the type of vesicle that is needed. This binding is predicated on the number and character of the functional target groups on the vesicle surface.

The synthetic processes employed in the manufacture of targeted vesicles for dental drug delivery systems have been expanded hereafter to include all other procedural variations that offer an array of targeting mechanisms which will selectively seek and bind to crystalline hydroxyapatite surfaces such as are found in tooth enamel and bone.

These methods produce dental delivery systems with maximal, as well as nominal, hydroxyapatite binding affinities.

The table, FIG. 2, is a list of the sample codes, lipid constituents, weights in mg., sonication and annealing times and temperatures and conditions under which the various vesicle preparations are made.

Each of the vesicle preparations outlined in FIG. 2 is treated as follows to produce the final vesicle product.

The lipid constituents are first solubilized in a solution of Chloroform-methanol (2:1 v/v) and then dried with slow rotation using a Buchi rotoevaporator and accompanying waterbath at 60° C.±0.5° C. The lipids are dried under pump vacuum for 15 minutes before being transferred to a vacuum desiccator and further dried for one hour at ambient temperature. Following the drying period each lipid crust is reconstituted with either an aqueous solution of glucose in water at a concentration of 1 mg/ml or 10 mM phosphate buffer at 7.4.

The lipid constituents are then sonicated in a cuphorn sonicator powered by a Heat Systems Model W 200R amplifier. The sonication and annealing procedures then proceed according to the schedule outlined in Table I. After the annealing procedure the samples are centrifuged in a Triac Clinical Centrifuge on the blood-setting mode for 15 minutes at ambient temperature. The supernatant is then chromatographed over a freshly prepared 1.5 cm×25 cm Sepharose CL-2B-300 column that has been equilibrated with 10 mM phosphate buffer at pH 7.4. Vesicle fractions are then evaluated for their lipid concentration based on ultraviolet light scattering and radiochemical analysis. Ultraviolet light is not absorbed by lipid vesicle but it is scattered. This refracted light shows up on a ultraviolet monitor as a light scattered signal which is subsequently recorded. The extent to which light is scattered is proportional to the peak height on the recorder. In FIG. 1, the core volume is shown as carbon 14. This material is not to be included in commercial product, but is used and illustrated for test purposes.

RESULTS

Figure 3:
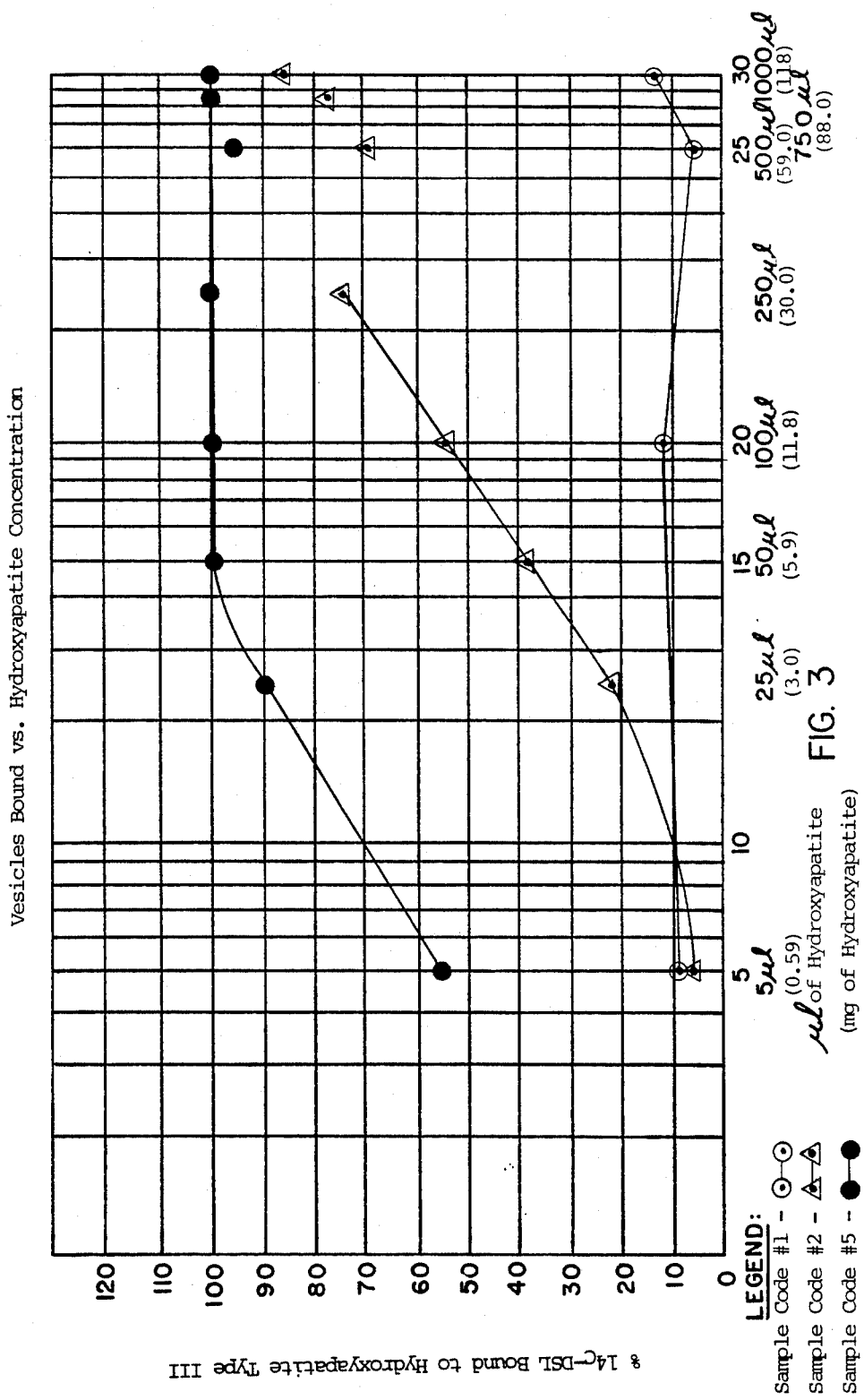
FIG. 3 illustrates the results of an experiment designed to study liposome binding to hydroxyapatite.

The vesicle sample codes and their lipid constituents are listed in FIG. 2 for easy reference to the following figures:

FIG. 3 illustrates the results of an experiment that was designed to study vesicle binding to hydroxyapatite (H.A.) (Type III, Sigma). Along the abscissa of the graph, increasing levels of hydroxyapatite are used to generate a hydroxyapatite crystal sink that is capable of being saturated with a given vesicle preparation. The degree of vesicle binding and subsequent hydroxyapatite saturation is measured by incorporating a radiolabeled $^{14}$C-DSL constituent into the vesicle membrane at the time of synthesis and then comparing the amount of radiolabel bound to hydroxyapatite versus the amount of radiolabel that is free in the supernatant following the centrifugation of hydroxyapatite crystals. The results graphed in FIG. 3 are expressed as a percentage of $^{14}$C bound relative to the hydroxyapatite concentration.

FIG. 3 shows that Sample Code #5, which contains chromium and Dequest in addition to the L-αphosphatidyl inositol-4,5-diphosphate group, has a greater binding affinity at any given concentration of hydroxyapatite than does the phosphatidyl inositol-4,5-diphosphate or the phosphatidyl glycerol moiety.

Phosphatidyl glycerol (PG) is also inserted in the vesicle membrane at the time of sonication, even though (PG) does not in this particular circumstance function as a connector molecule. However, it occupies the same spatial or three-dimensional position as a connector molecule. Phosphatidyl glycerol is an example of a molecule that shows weak binding affinity to hydroxyapatite at all concentrations of hydroxyapatite tested. It can be concluded that Sample Code #1 with phosphatidyl glycerol present in the vesicle membrane is a good control vesicle with insignificant hydroxyapatite binding affinity.

Intermediate between Sample Code #5 (Chromium-Dequest) and Sample Code #1 (Phosphatidyl glycerol) is Sample Code #2 with L-αphosphatidyl inositol-4,5-diphosphate present as the functional binding molecule occupying the connector molecule position. L-αphosphatidyl inositol-4,5-diphosphate has two opposed phosphated groups in positions #4 and #5 on the inositol ring structure that serve to bind to the crystalline lattice of hydroxyapatite. These phosphate groups can also bind to chromium ions. Furthermore, phosphatidyl inositol-4,5-diphosphate is not capable of more than 86% binding capacity as defined by the parameters of the experimental results shown in FIG. 2. Thus, phosphatidyl inositol-4,5-diphosphate appears to be intermediate between chromium-Dequest and phosphatidyl glycerol in its binding affinity for hydroxyapatite.

Figure 4:
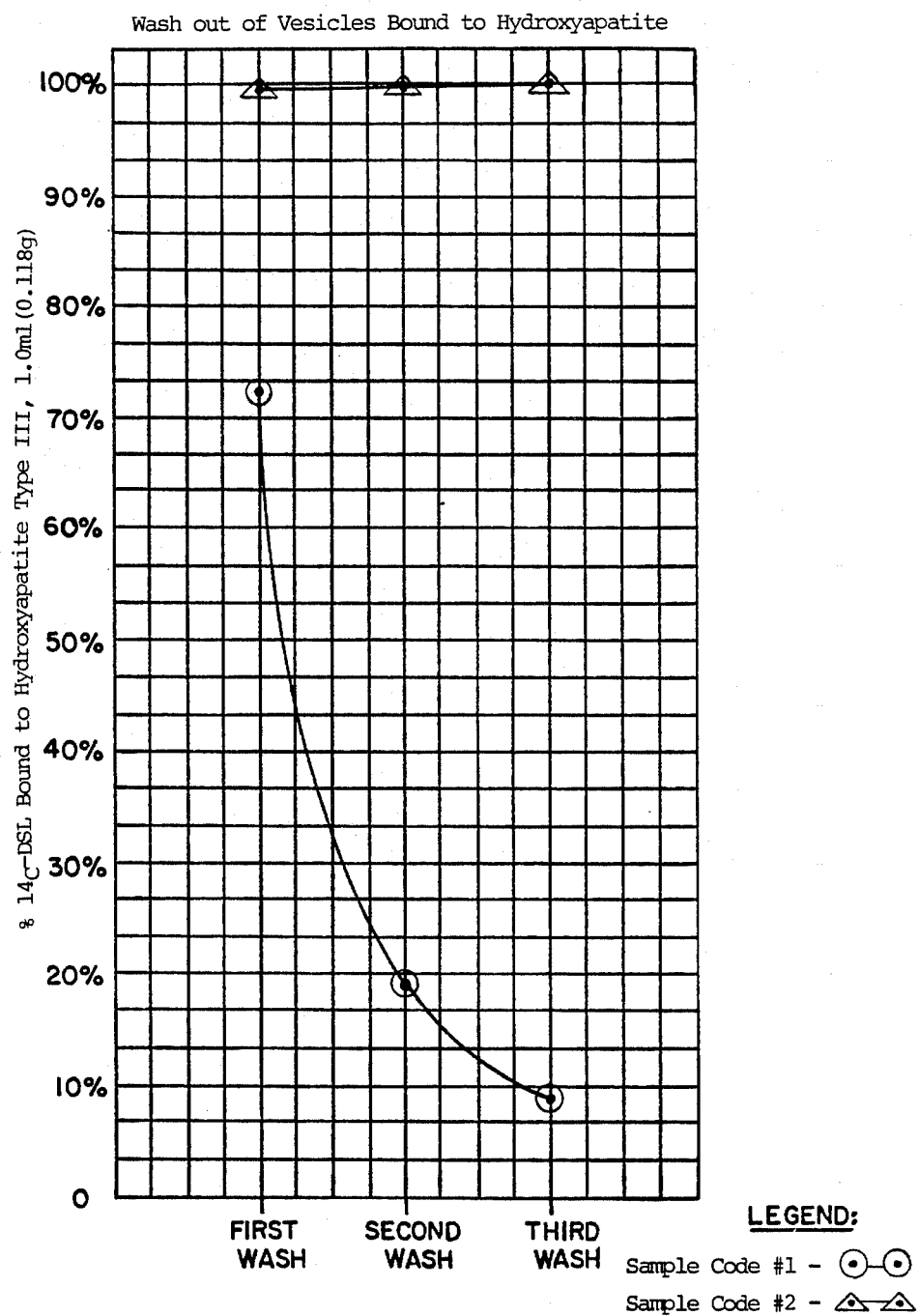
FIG. 4 depicts the results of an experiment designed to wash away free or loosely held liposomes on the hydroxyapatite surface.

FIG. 4 depicts the results of an experiment designed to wash away any free or loosely held vesicles on the hydroxyapatite surface. Once again, the percent of $^{14}$C-DSL that is bound is measured in the same manner as observed for the experiment illustrated in FIG. 3.

The vesicles with the L-αphosphatidyl inositol-4,5-diphosphate groups on the vesicle surface bind to hydroxyapatite very well and near 100% capacity, even after three consecutive equal volume washes with 10 mM potassium phosphate buffer, pH 7.4. However, the vesicles with simply phosphatidyl glycerol on their surface are washed off the hydroxyapatite rather rapidly, as shown with the washout curve in FIG. 4. Only 9% of the original vesicles remain after three consecutive washes of the hydroxyapatite.

Figure 5:
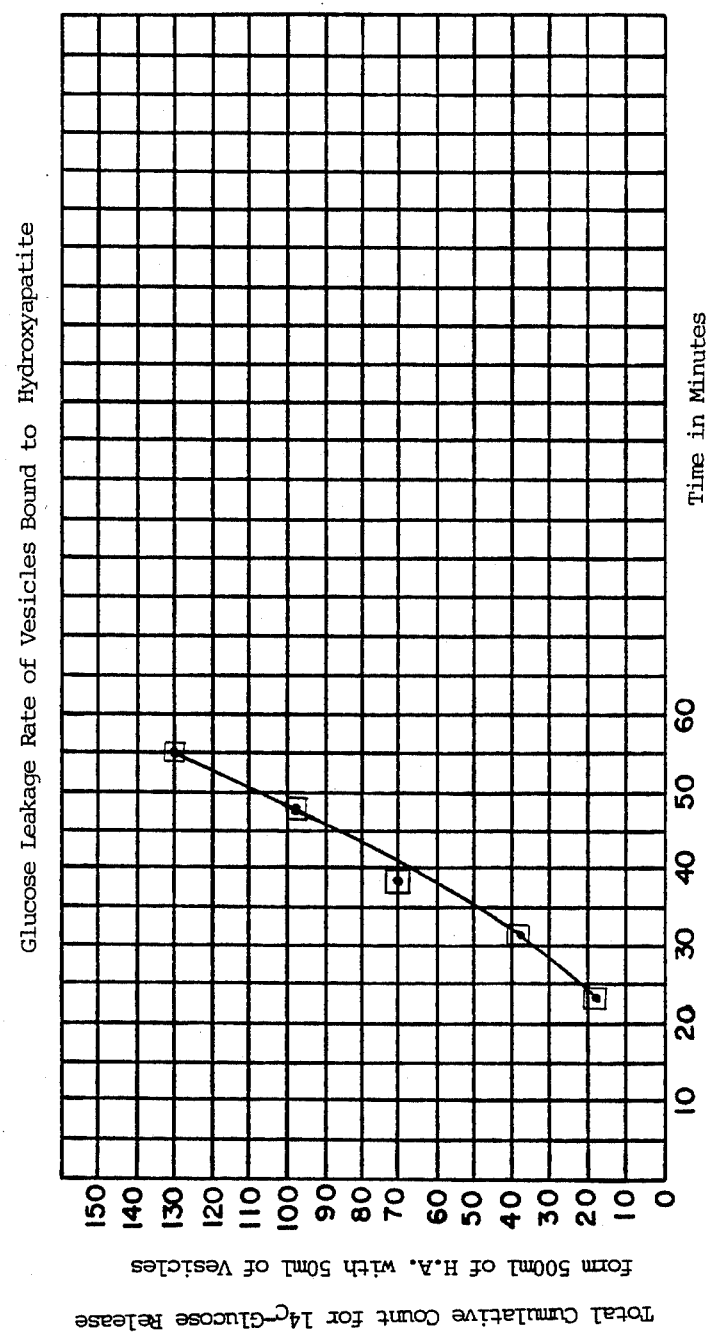
FIG. 5 illustrates that events that occur when liposomes are bound to hydroxyapatite and allowed to leak their core volume contents over time into the external media.

FIG. 5 demonstrates the events that occur when vesicles which contain L-αphosphatidyl inositol-4,5-diphosphate are bound to hydroxyapatite and allowed to leak their soluble $^{14}$C core volume contents over time into the external media.

FIG. 3 shows that vesicles with the phosphatidyl inositol-4,5-diphosphate moiety bind convincingly to hydroxyapatite. Thus, for the experiment shown in FIG. 5, it can be assumed that the phosphatidyl inositol-4,5-diphosphate vesicles are bound substantially to the hydroxyapatite. The physical event which is concomitantly observed after binding is the continual and cumulative leakage of $^{14}$C-glucose from the core volume as a function of time.

In a separate experiment, Sample Code #4, with $^{14}$C-glucose-DSL-CHOL L-αphosphatedyl inoselot +4,5-diphosphate was observed to bind to a single human tooth which was immersed in a vesicle suspension for 15 minutes at ambient temperature. In this preliminary experiment, 18.1% of the available vesicles bound to the crystalline surface of the tooth in 10 mM phosphate buffer, pH 7.4.

Experimentally 50 μl of the stock vesicle preparation from Sample Code 190 4 was added to 650 μl of 10 mM potassium phosphate buffer, pH 7.4, to form the incubation medium. At the concentration of lipid vesicles used in this experiment, it is likely that a vesicle monolayer was chemisorbed to the tooth, signaling that a maximum level of vesicle saturation was achieved within the parameters of the experiment.

In summary, it can be concluded that maximal binding to hydroxyapatite is achieved with the Dequest binding molecule, and that by altering the mole ratio of lipid constituents in the vesicle membrane the core volume contents can be made to leak at designated and variable rates.

What is claimed is:

1. A composition of matter for prolonged oral administration to a warm blooded animal of dental therapy and oral cavity breath freshener chemicals, comprising:
    a first component which is a tooth structure protective and therapeutic chemical or cosmetic breath freshener, said first component being encapsulated in or associated with;
    a second component which comprises lipid membrane structures in the form of vesicles; and
    a third component which is a molecule having a fatty substituent attached to the vesicle wall and a target substituent selected from the class consisting of chemicals which are classed biologically as having affinity for hydroxyapatite.

2. The composition of matter as claimed in claim 1 wherein the third component target substituents are chemicals which are classed biologically as hydroxyapatite attracted being selected from the class consisting of diphosphonates, polyphosphoinositides and carboxylic acids.

* * * * *